US006287284B1

(12) United States Patent
Warburton-Pitt

(10) Patent No.: US 6,287,284 B1
(45) Date of Patent: *Sep. 11, 2001

(54) SILICONE BAG ASSEMBLY

(75) Inventor: Stephen Warburton-Pitt, Andover, NJ (US)

(73) Assignee: NPT, Inc., Wayne, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/406,586

(22) Filed: Sep. 27, 1999

(51) Int. Cl.[7] .................................................. A61M 5/00
(52) U.S. Cl. ......................................... 604/257; 604/408
(58) Field of Search .................................. 604/403–416, 604/257, 262; 206/363, 210, 438, 571; 428/12, 33, 34.1, 35.2, 35.4, 35.7, 36.6, 36.7

(56) References Cited

U.S. PATENT DOCUMENTS 4,573,992 * 3/1986 Marx .................................. 604/408
6,019,751 * 2/2000 Gabbard et al. .................... 604/408

* cited by examiner

*Primary Examiner*—Anhtuan T. Nguyen
*Assistant Examiner*—Michael M. Thompson
(74) *Attorney, Agent, or Firm*—David L. Davis

(57) ABSTRACT

The combination of a bag and tubes connected thereto for use in pharmaceutical manufacturing and for holding health care related solutions is formed entirely of silicone. This avoids the previous problem of the releasing into the held fluids of plasticizers or plastic additives contained in the PVC material making up prior bags.

7 Claims, 3 Drawing Sheets

SILICONE BAG ASSEMBLY

BACKGROUND OF THE INVENTION

This invention relates to a bag assembly for use in pharmaceutical manufacturing and for holding health care related solutions and, more particularly, to an improved bag assembly manufactured of silicone.

At the present time, virtually all bags used by the pharmaceutical industry and for holding health care related solutions (such as intravenous bags) are manufactured of polyvinyl chloride (PVC). PVC is a commonly used inexpensive plastic material which is naturally hard. To soften such material so that it can be used as a flexible bag and as flexible tubing, plasticizers such as phthalate esters are added to the PVC to soften it. Recently there has been concern that phthalates may leach from the PVC to which they have been added, thereby contaminating aqueous fluids held in PVC bags and traveling through PVC tubing. Since PVC bags are used to store intravenous solutions and blood for transfusions, phthalates which leach from the PVC are infused directly into a patient's bloodstream. It would therefore be desirable to have a phthalate-free bag and tubing for such purposes.

SUMMARY OF THE INVENTION

It is known that silicone is a relatively inert chemical in aqueous solutions, i.e., it does not react with contacting liquids or leach chemicals into contacting liquids. Accordingly, the present invention provides the combination of at least one silicone tube having an open central passageway and a flexible silicone membrane formed into a tubular shape with opposed ends. The membrane tubular shape is larger in diameter than the tube. Each tube extends into a respective end of the membrane so that the respective open central passageway of the tube is in communication with the interior of the tubular shaped membrane. Each of the membrane ends is flattened and sealed to itself and to a respective tube, thereby forming a bag assembly.

In accordance with an aspect of this invention, the flexible silicone membrane is formed as a seamless tube.

In accordance with another aspect of this invention, the flexible silicone membrane is a silicone sheet having opposed edges overlapped and joined together so that the membrane attains a tubular configuration.

BRIEF DESCRIPTION OF THE DRAWINGS

The foregoing will be more readily apparent upon reading the following description in conjunction with the drawings in which like elements in different figures thereof are identified by the same reference numeral and wherein.

DETAILED DESCRIPTION

Figure 1:
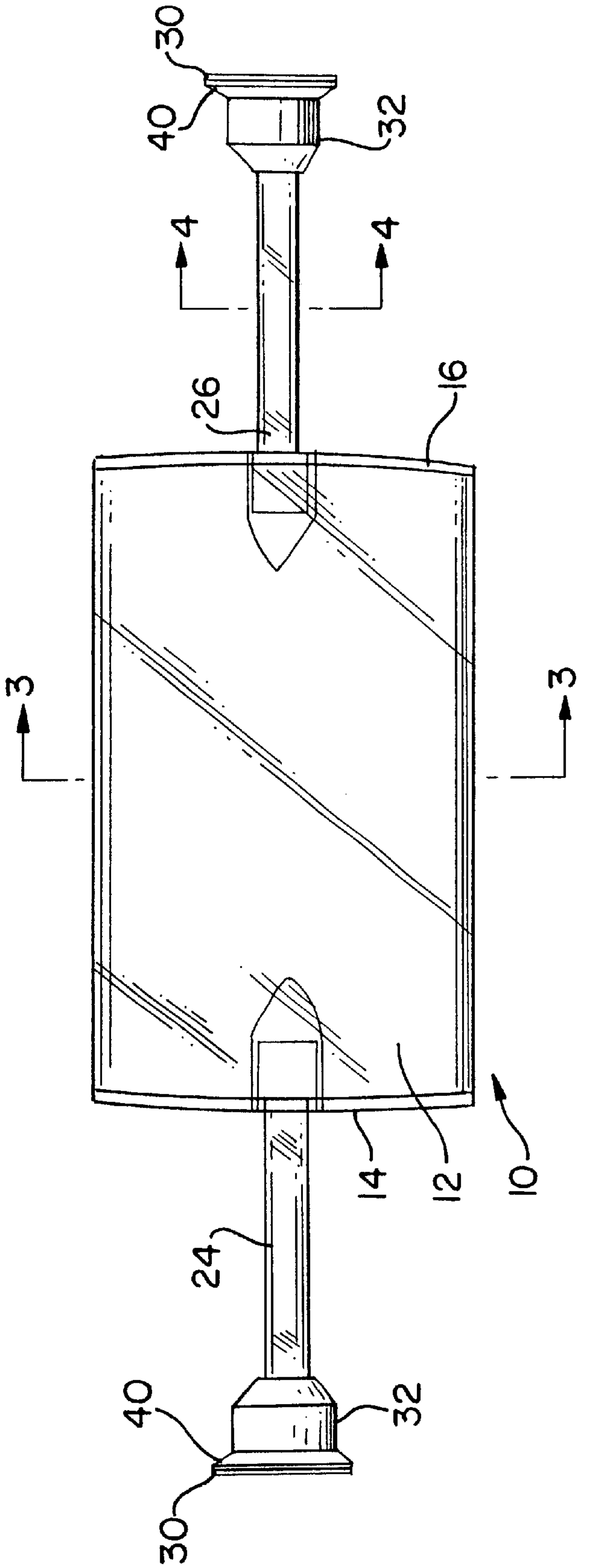
FIG. 1 is a plan view of a first embodiment of the present invention.
Figure 2:
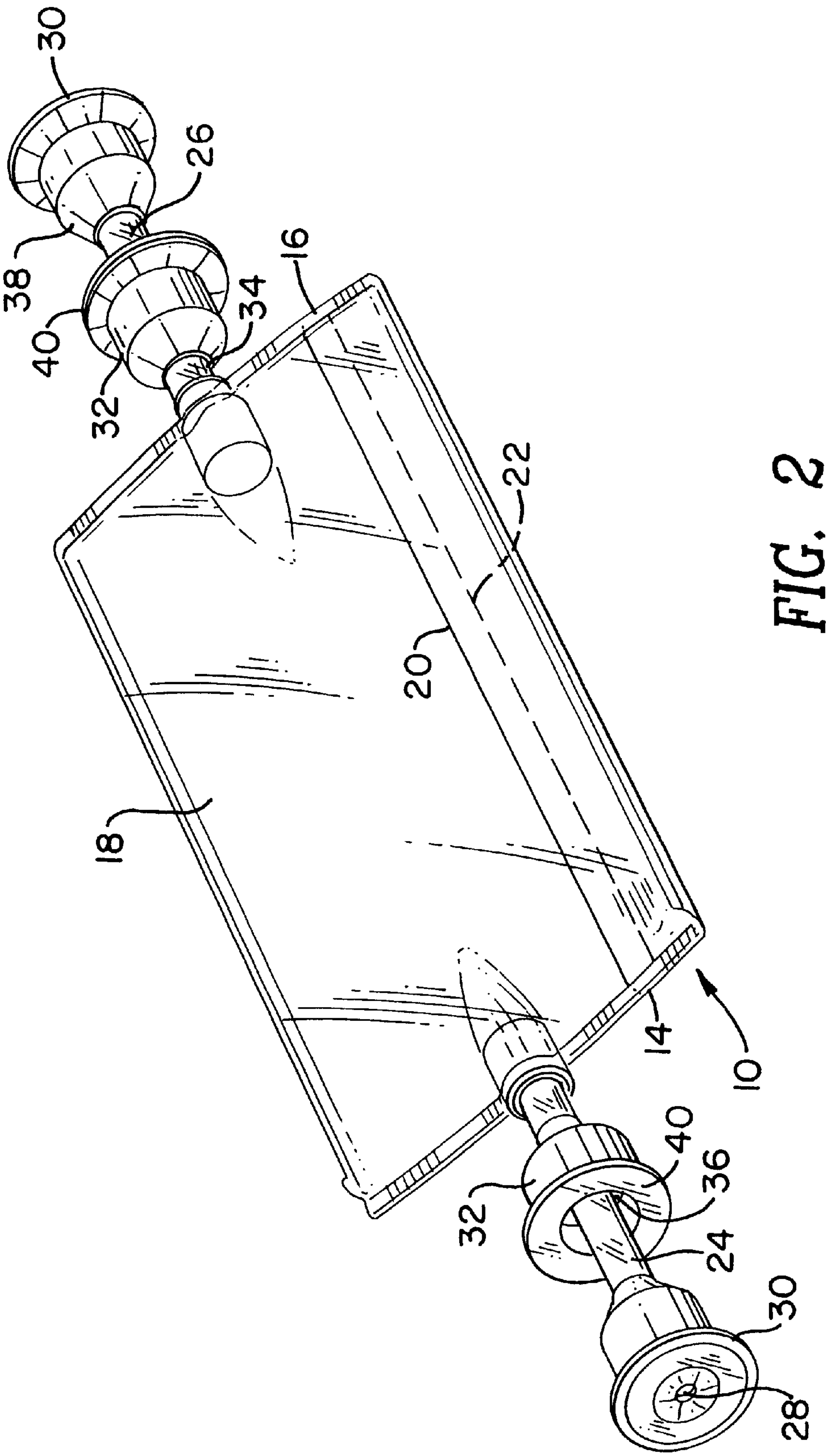
FIG. 2 is a perspective view of an alternate embodiment of the present invention.
Figure 3:
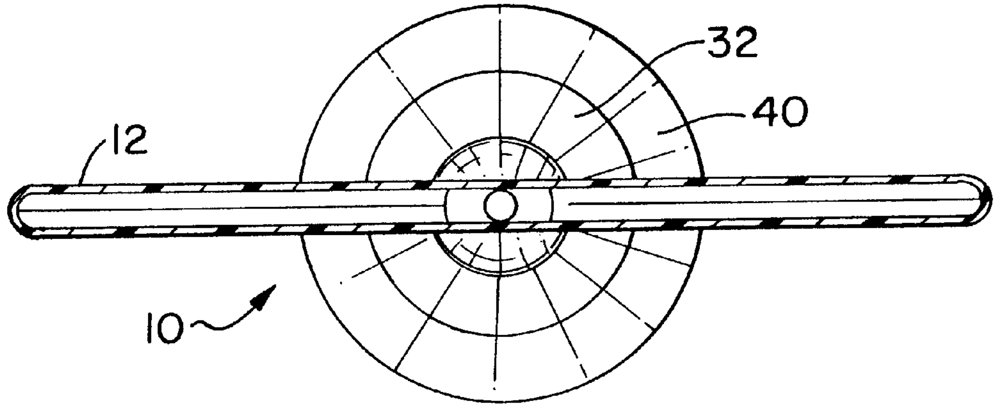
FIG. 3 is a cross sectional view taken along the line 3—3 in FIG. 1.

Referring now to the drawings, FIG. 1 shows a first embodiment of a combination of a silicone bag and tubes constructed according to the present invention. As shown, the inventive combination, designated generally by the reference numeral 10, includes a flexible silicone membrane 12 which is formed as a seamless thin-walled tube having opposed ends 14, 16. The difference between the embodiment shown in FIG. 1 and the embodiment shown in FIG. 2 is that in FIG. 2, the membrane 18 is originally a sheet and is formed into a tubular shape by having its opposed edges 20, 22 overlapped and joined together, as by adhesive or the like, to attain a tubular configuration. (Liquid silicone is a preferred adhesive.) In all other respects, the embodiments shown in FIGS. 1 and 2 are identical.

Figure 4:
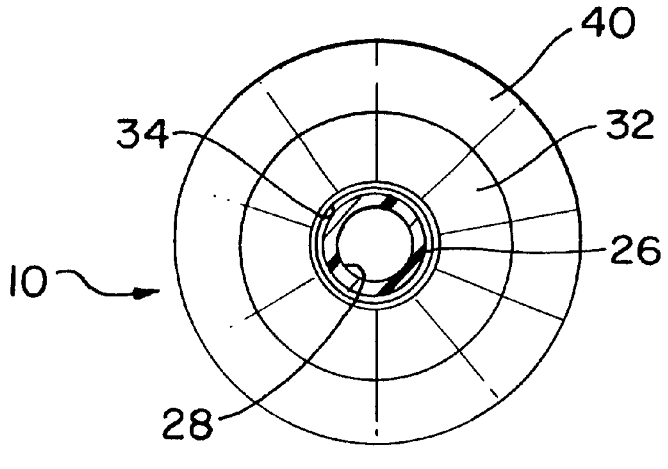
FIG. 4 is a cross sectional view taken along the line 4—4 in FIG. 1.

The inventive combination 10 also includes a pair of silicone tubes 24, 26. Each of the tubes 24, 26 has an open central passageway 28 (FIG. 4). The wall of each of the tubes 24, 26 is considerably thicker than the membrane 12, so that each tube 24, 26 is not as flexible as the membrane 12.

The tubular shape of the membrane 12 is larger than the diameter of each of the tubes 24, 26 (which are preferably, but not necessarily, equal in size) and each of the tubes 24, 26 extends into a respective one of the opposed ends 14, 16 of the membrane 12 so that the respective open central passageway 28 of each tube 24, 26 is in communication with the interior of the tubular shaped membrane 12. Preferably, the tubes 24, 26 are arranged substantially coaxially. Each of the ends 14, 16 of the membrane 12 is flattened and sealed to itself and to a respective one of the tubes 24, 26, as by adhesive or the like. Thus, the membrane 12 forms a compartment, or bag, of variable capacity. The maximum capacity of a bag is determined by the spacing between the opposed ends 14, 16 and by the diameter of the tube formed by the membrane 12, 18.

At the distal end of each of the tubes 24, 26 remote from the membrane 12, the tube is terminated by a silicone flange 30 surrounding the open central passageway 28. A stainless steel backup cup 32 having a central bore 34 is slidably mounted on each of the tubes 24, 26. The backup cup 32 has an inner surface portion 36 which is complemental to the surface 38 of the flange 30 which faces the membrane 12. The surface 36 of the backup cup 32 is terminated by a flange 40. Thus, the backup cups 32 provide support for the flanges 30 and allow a pair of tubes 24, 26 to be coupled together by clamps secured to the flanges 40, holding the flanges 30 so that there is communication between the passageways 28 of the tubes which are coupled together.

The assembly 10 can be constructed to have any desired capacity. As presently contemplated, the capacity will probably be in the range from about 750 ml up to about 5 liters, but larger capacity assemblies, even up to one thousand liters, are within the scope of this invention. Further, the assembly 10 is not limited to any specific use, although it is presently contemplated that it will be used for storage (and cryogenic shipment) of intermediate or concentrated drug products during manufacture in an industrial setting.

Accordingly, there has been disclosed an improved bag assembly for use in pharmaceutical manufacturing and for holding health care related solutions which does not release any plasticizers or plastic additives into the solutions. While illustrative embodiments of the present invention have been disclosed herein, it is understood that various modifications and adaptations to the disclosed embodiments are possible and it is intended that this invention be limited only by the scope of the appended claims.

What is claimed is:

1. In combination:

at least one silicone tube having an open central passageway and terminated at its distal end by a silicone flange surrounding the open central passageway; and a flexible silicone membrane formed into a tubular shape with an interior and opposed ends;

wherein the membrane tubular shape is larger in diameter than the at least one tube, each of the at least one tube extends into a respective end of the membrane so that the respective open central passageway of the tube is in communication with the interior of the tubular shaped membrane, and each of the membrane ends is flattened and sealed to itself and to a respective one of the at least one tube;

and further comprising for each of said at least one tube:

a backup cup mounted on the tube and having a surface portion complemental to the surface of the flange facing the membrane;

whereby a pair of tubes can be coupled together by clamping their respective backup cups.

2. The combination according to claim 1 wherein:

said flexible silicone membrane is formed as a seamless tube.

3. The combination according to claim 1 wherein:

said flexible silicone membrane is a silicone sheet having opposed edges overlapped and joined together so that said membrane attains a tubular configuration.

4. The combination according to claim 1 wherein said at least one silicone tube consists of two silicone tubes arranged substantially co-axially at opposite ends of the membrane.

5. The combination according to claim 1 wherein the backup cup is formed of a rigid material.

6. The combination according to claim 5 wherein the rigid material is a metal.

7. The combination according to claim 6 wherein the metal is stainless steel.

* * * * *